United States Patent
Maschke

(10) Patent No.: US 7,993,361 B2
(45) Date of Patent: Aug. 9, 2011

(54) DEVICE FOR REMOVING A TOTAL VASCULAR OCCLUSION WITH OCT MONITORING

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 1683 days.

(21) Appl. No.: 11/093,451

(22) Filed: Mar. 30, 2005

(65) Prior Publication Data

US 2005/0222595 A1    Oct. 6, 2005

(30) Foreign Application Priority Data

Mar. 31, 2004 (DE) .......... 10 2004 015 642

(51) Int. Cl.
*A61M 29/00* (2006.01)
(52) U.S. Cl. .................................................. 606/191
(58) Field of Classification Search .......... 606/159, 606/190–200
See application file for complete search history.

(56) References Cited

U.S. PATENT DOCUMENTS

| | | | |
|---|---|---|---|
| 5,193,546 A | | 3/1993 | Shaknovich |
| 5,549,551 A | * | 8/1996 | Peacock et al. .......... 604/103.05 |
| 5,741,270 A | | 4/1998 | Hansen et al. |
| 5,827,313 A | * | 10/1998 | Ream .......................... 606/171 |
| 5,906,579 A | * | 5/1999 | Vander Salm et al. ........ 600/424 |
| 5,921,926 A | | 7/1999 | Rolland et al. |
| 6,066,102 A | * | 5/2000 | Townsend et al. ............ 600/564 |
| 6,120,516 A | * | 9/2000 | Selmon et al. ................ 606/159 |
| 2001/0018596 A1 | * | 8/2001 | Selmon et al. ................ 606/198 |
| 2006/0120516 A1 | | 6/2006 | Armbruster et al. |

FOREIGN PATENT DOCUMENTS

| | | |
|---|---|---|
| EP | 0 815 801 B1 | 1/1998 |
| EP | 0 885 594 B1 | 12/1998 |
| JP | 11319106 A | 11/1999 |
| JP | 2002502674 A | 1/2002 |
| JP | 2002214127 A | 7/2002 |
| WO | WO 01/11409 A2 | 2/2001 |

OTHER PUBLICATIONS

Frontrunner™ CTO Catheter, LuMend, Inc., [Retrieved on Mar. 30, 2005], Retrieved from [online],. http://www.lumend.com/Products.html.

* cited by examiner

*Primary Examiner* — Darwin P Erezo
*Assistant Examiner* — Gregory Anderson

(57) ABSTRACT

Device for removing a total vascular occlusion with the aid of a CTO catheter with expansion tongs arranged at the front end and OCT monitoring, the CTO catheter being combined with an OCT catheter to form an integrated unit.

7 Claims, 3 Drawing Sheets

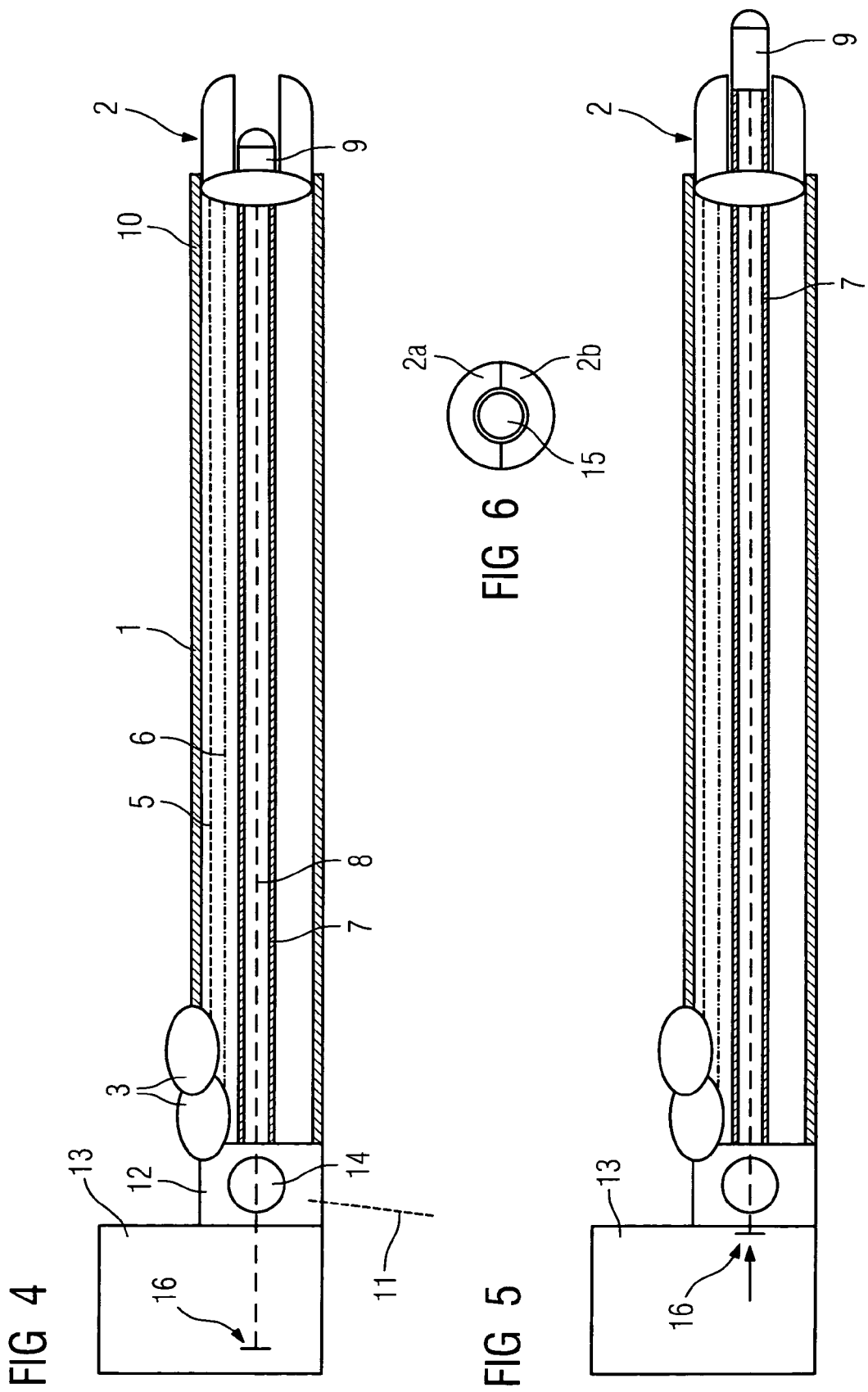

DEVICE FOR REMOVING A TOTAL VASCULAR OCCLUSION WITH OCT MONITORING

CROSS REFERENCE TO RELATED APPLICATION

This application claims priority of the German application No. 10 2004 015 642.5 DE filed Mar. 31, 2004, which is incorporated by reference herein in its entirety.

FIELD OF THE INVENTION

The invention relates to a device for removing a total vascular occlusion using a CTO catheter with expansion tongs arranged at the front end and OCT monitoring.

BACKGROUND OF THE INVENTION

Among the most common fatal diseases are vascular diseases, in particular cardiac infarction. This is caused by disease of the coronary vessels (atherosclerosis). Deposits (atherosclerotic plaque) thereby cause a blockage of the coronary vessels. In particularly serious cases this can lead to total occlusion of the coronary vessels or chronic total coronary occlusion (CTO). In the past such occlusions could generally only be treated by means of a bypass operation. In recent years laser angioplasty (PTLA) has also become established as a method for removing plaque, particularly in the case of long stenoses (>2 cm) and total occlusion. However with PTLA there is a not insignificant risk of injury in the form of hemorrhage, damage or perforation/dissection of the vascular wall.

In February 2002 a new instrument—a so-called CTO catheter—was licensed by the FDA for the removal of chronic total occlusions. This device operates in a similar fashion to expansion tongs by applying pressure to break up the plaque in the coronary vessels bit by bit, thereby allowing gradual removal of the total vascular occlusion. Such a CTO catheter for removing a chronic total occlusion is for example disclosed in'U.S. Pat. No. 5,741,270 "Manual Actuator for a Catheter System for Treating a vascular occlusion" and in U.S. Pat. No. 6,120,516 "Method for Treating Vascular Occlusion" in particular FIG. 18. A known product is the Frontrunner CTO catheter from LuMend, Inc., Redwood City, Calif.

Intervention with the CTO catheter is carried out subject to X-ray control with an angiography system. The disadvantage of this method is that the coronary vessels are only displayed as two-dimensional and only the actual constriction is shown in the X-ray image. In order to show the vessel clearly, contrast agents also have to be injected into the coronary vessels. Some patients are known to be allergic to contrast agents and some patients report a sudden hot sensation. Also it is difficult for medical personnel to distinguish between plaque and vascular wall during the intervention. This increases the risk of the expansion tongs being deployed in the wrong place, resulting in injury to the vascular wall.

Insertion of an IVUS catheters (Intravascular Ultrasound) into the vessel improves the imaging information but has the disadvantage that a relatively expensive catheter also has to be inserted into the patient and must be removed from the vessel before insertion of the CTO catheter. An IVUS system is for example disclosed in EP 0 885 594 B1 and in U.S. Pat. No. 5,193,546.

Significantly better local resolution, particularly in the relevant close-up range, is provided by an OCT catheter (Optical Coherence Tomography), which is inserted separately into the vessel. The OCT method is for example disclosed in WO 01/11409 A2, in U.S. Pat. No. 5,921,926 and in EP 0 815 801 B1. This technique operates in a similar fashion to imaging ultrasound (B mode). The essential physical principle is based on the Michelson interferometer. The disadvantage of this method is that the OCT device has to be withdrawn from the vessel whenever the CTO catheter is inserted.

SUMMARY OF THE INVENTION

The object of the invention is therefore to configure a device of the type mentioned above such that an optimal, easy to operate device is provided, with which the intervention site can be directly observed even as the vessel is being extended, without complex swapping of the various catheters.

To achieve this object, according to the invention the CTO catheter is combined with an OCT catheter to form an integrated unit, with rotating OCT signal lines preferably arranged in the tubular catheter sheath of the OCT catheter in addition to the mechanical actuation lines to the expansion tongs, said OCT signal lines running to an OCT sensor, in particular a rotating mirror, that can be arranged inside a circumferential annular window directly behind the expansion tongs or that can be moved through an opening in the expansion tongs to be arranged directly in front of them.

The configuration according to the invention results in an integrated unit comprising a CTO catheter with an OCT catheter integrated therein, which represents an optimum system for opening up total vascular stenoses. The major advantage of the solution is the reduction in the number of method steps and the reduction in the number of catheters used, as well as the reduction in exposure to X-ray radiation. The images of the OCT system provide important additional medical information with a high resolution, in particular in the close-up range, about the plaque and the vascular wall. The plaque can thereby be identified in each instance and plaque removal can be carried out at the correct sites using the CTO expansion tongs and a successful outcome can then be verified immediately, without unnecessarily high exposure of the patient to contrast agents or X-rays. The risk of injury to the vascular wall is also reduced.

In a development of the invention the OCT signal line, which is preferably configured as a glass fiber line, can be located inside a hollow, flexible drive shaft for the OCT sensor.

To arrange the OCT sensor in front of the expansion tongs, thereby allowing direct observation of the total stenosis before the start of treatment, the drive shaft for the OCT sensor with the OCT signal lines running through it should be supported in the CTO catheter sheath such that it can be advanced through the opening already discussed in the center of the expansion tongs. After a first observation of the total stenosis the OCT sensor is withdrawn in the CTO catheter sheath so that the expansion tongs can be deployed. The sensor can then be advanced again to observe the outcome of the work and so on so that the total vascular stenosis can gradually be opened up.

According to a further feature of the present invention, the CTO catheter sheath should also be provided with inlet or outlet openings at its ends for a contrast agent or a rinsing fluid, so that the intervention area to be observed in each instance can be rinsed clean, thereby allowing better observation.

In addition to magnets that can be arranged in the region of the tip of the CTO catheter for magnetic navigation in the vessel, there can optionally also be provision for a preferably multi-chamber, inflatable balloon to be arranged at the tip of the CTO catheter to hold the catheter in the vessel and/or to dilate the vessel.

Finally it is also within the scope of the invention that the device has a guide wire or guide catheter running through it.

A typical method sequence when using a device according to the invention is as follows:

Insertion of a guide wire or guide catheter subject to X-ray control, in some instances with contrast agent, into the target position (stenosis).

Insertion of the integrated CTO-OCT catheter subject to X-ray control, in some instances with contrast agent, into the target position.

Once in the required target position the rinsing fluid for the OCT method is injected and the site from which the plaque is to be removed is observed at high resolution.

The CTO intervention is then carried out gradually in the plaque, with the option of verifying progress using OCT after each dilation process.

Once the full intervention has been completed, the complete vessel segment is checked once again using OCT. In addition to the combined CTO-OCT catheter discussed above, the device according to the invention also has a unit to link the proposed catheter to a user interface for the part of the integrated catheter used to remove the plaque. In addition to a signal interface unit and a preprocessing stage for the OCT image data, an image processing and image display unit is provided with an image storage unit. A power supply unit and network interface are of course also present.

The OCT image system can be extended to include menus to allow quantification of the stenosis to be removed, for example the extent of the stenosis before and after intervention. The user interface can also have input options so that patient data and data for the catheter parameters can be input using a keyboard and/or barcode or a mouse.

BRIEF DESCRIPTION OF THE DRAWINGS

Further advantages, features and details of the invention will emerge from the description which follows of some exemplary embodiments and with reference to the drawing, in which:

FIGS. 4 and 5 show schematic diagrams of a modified exemplary embodiment of a combined CTO-OCT catheter according to the invention in different operating positions of the OCT sensor that can be advanced through the expansion tongs and FIG. 6 shows an enlarged front view of the tip of the CTO catheter with the opening for advancing the OCT sensor.

DETAILED DESCRIPTION OF THE INVENTION

Figure 1:
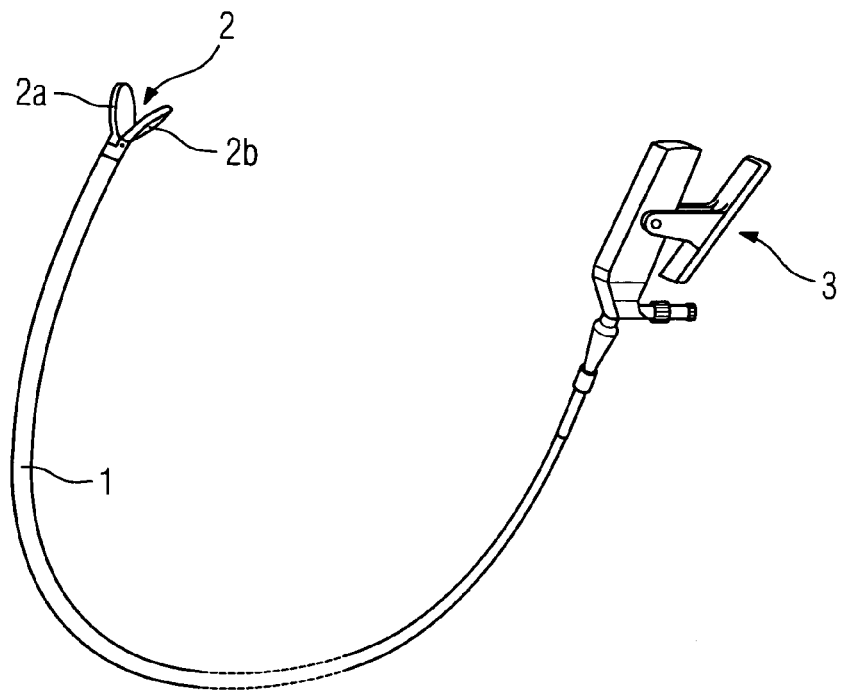
FIG. 1 shows a diagram of a CTO catheter.
Figure 2A:
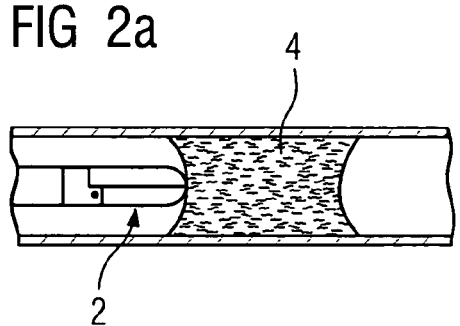
FIGS. 2a to 2d show schematic diagrams of the removal of a total stenosis using such a CTO catheter at different points of the intervention.
Figure 2B:
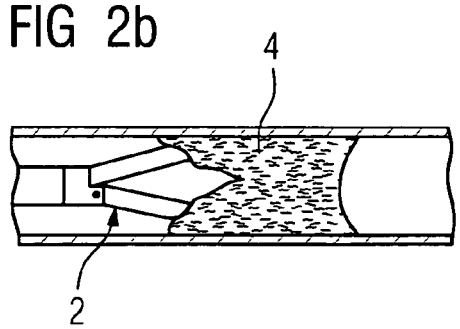
Figure 2C:
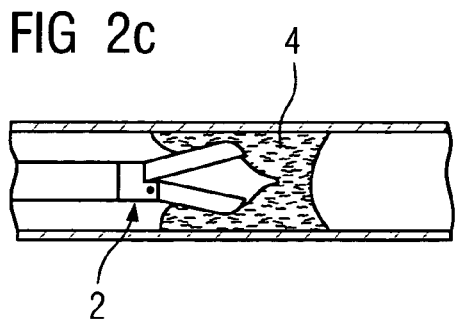
Figure 2D:
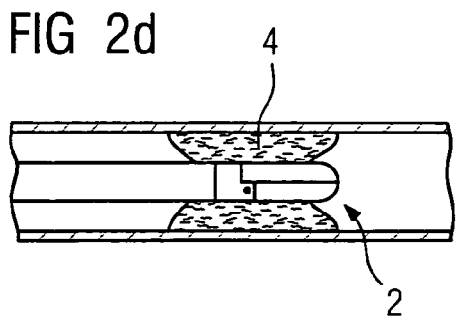

FIG. 1 shows a CTO catheter with a flexible catheter sheath 1, at the tip of which expansion tongs 2 are arranged, which can be operated by way of the similarly tong-type handle 3, so that they can be opened up from the closed position of the tong arms 2a and 2b as shown in FIGS. 2a and 2d to the open position as shown in FIGS. 2b and 2c, which show different stages of the opening up of the plaque 4.

Figure 3:
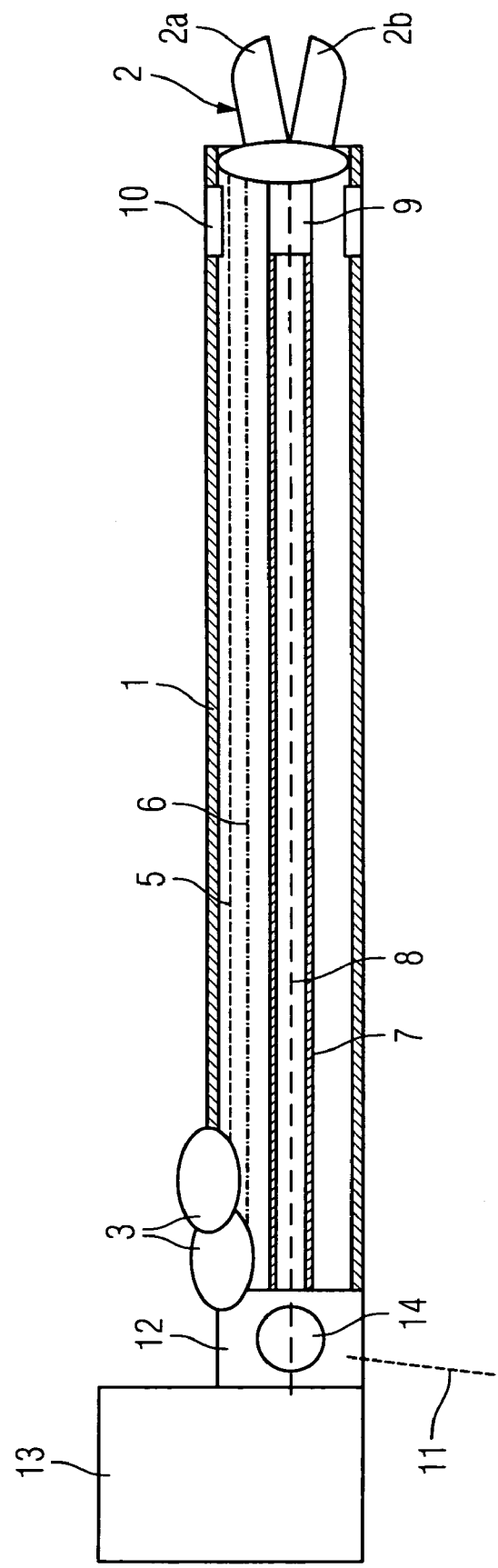
FIG. 3 shows a schematic view of the structure of a combined CTO-OCT catheter according to the invention with an OCT sensor arranged directly behind the expansion tongs.

FIG. 3 shows a schematic diagram of the basic structure of the CTO catheter with integrated OCT monitoring according to the invention for use in stenosis removal. Actuation lines 5 and 6 are provided inside the flexible catheter sheath 1, running from the actuation handle 3 to the expansion tongs, one of the lines bringing about the opening movement of the tong arms and the other line their closing movement. This can be achieved by way of flexible tongs or more simply by tension wires. As well as the actuation lines 5 and 6, the flexible catheter sheath 1 also contains a hollow flexible drive shaft 7 with glass-fiber signal lines 8 arranged therein for an OCT sensor 9 preferably configured as a mirror, which is arranged directly behind the expansion tongs inside a transparent annular window 10 in the catheter sheath 1. 11 shows a link for contrast agents and rinsing fluid, which can be pumped through the catheter sheath 1 to an outlet opening (not shown) arranged in the region of the annular window 10. The combined catheter is connected via the mechanical connecting system 12 to the signal interface and the drive unit for the OCT system, shown in a simplified fashion by the box 13. This mechanical connecting system 12 contains a rotary coupling 14 for the links.

FIGS. 4 and 5 show a modified embodiment of a CTO-OCT catheter according to the invention, in which the OCT sensor 9 is not arranged behind the expansion tongs 2 but can be moved through an opening 15 in the expansion tongs, so that it can be advanced from the working position shown in FIG. 4 in which the tongs are actuated into the observation position according to FIG. 5. Otherwise the structure is identical to that of the exemplary embodiment according to FIG. 1.

The withdrawal and advancing of the hollow flexible drive shaft 7 for the OCT sensor with the OCT glass-fiber arranged therein is shown schematically by 16.

The invention is not restricted to the exemplary embodiments shown. Magnetic navigation would therefore also be possible, with permanent magnets or alternatively electromagnets on the catheter tip or on the catheter, said magnets and their positions not being shown in the figures. An inflatable balloon, preferably even with a plurality of chambers, could also be arranged in the region of the tip, to position or hold the catheter tip in the required position during the intervention and also to be deployed as a dilation balloon if required. This balloon is not shown in the drawings either. Also X-ray markers known per se could be provided on the catheter shaft and also of course openings for a guide wire. Finally it should be noted that the proposed solution of a combined CTO-OCT catheter for removing total stenoses is not restricted to use in coronary vessels but is essentially suitable for all types of vessels in the body.

The invention claimed is:

1. A device for removing a total vascular occlusion, comprising:
   a catheter sheath having a front end;
   a hollow, flexible drive shaft disposed within the catheter sheath,
   an OCT sensor disposed on the front end of the catheter sheath; and
   expansion tongs having an opening therethrough disposed at the front end of the catheter sheath;
   wherein the flexible hollow drive shaft accommodates signal lines for the OCT sensor alongside actuation lines for the expansion tongs; and
   wherein the OCT sensor is movable through the opening of the expansion tongs from an idle position disposed between the expansion tongs to an observation position wherein the OCT sensor is disposed forward of the expansion tongs.

2. The device according to claim 1, wherein the OCT sensor is a rotating mirror.

3. The device according to claim 1, wherein the OCT signal line is preferably configured as a glass-fiber line.

4. The device according to claim 1, wherein the catheter sheath is provided with inlet and outlet openings located at a rear end and the front end of the device for a contrast agent or a rinsing fluid.

5. The device according to claim 1, wherein magnets for magnetic navigation in a vessel are arranged in the region of at a tip of the device.

6. The device according to claim 1, wherein a preferably multi-chamber inflatable balloon is arranged at the tip of the device to hold the device in a vessel and for vessel dilation.

7. The device according to claim 1, wherein the device has a guide wire or guide catheter running through it.

* * * * *